United States Patent
Toller et al.

(10) Patent No.: US 10,048,494 B2
(45) Date of Patent: Aug. 14, 2018

(54) PROTECTION OF LASER BOND INSPECTION OPTICAL COMPONENTS

(71) Applicants: Steven M. Toller, Upper Arlington, OH (US); David Sokol, Dublin, OH (US); Mark E. O'Loughlin, Galloway, OH (US); Jeff L. Dulaney, Delaware, OH (US)

(72) Inventors: Steven M. Toller, Upper Arlington, OH (US); David Sokol, Dublin, OH (US); Mark E. O'Loughlin, Galloway, OH (US); Jeff L. Dulaney, Delaware, OH (US)

(73) Assignee: LSP TECHNOLOGIES, INC., Dublin, OH (US)

( * ) Notice: Subject to any disclaimer, the term of this patent is extended or adjusted under 35 U.S.C. 154(b) by 138 days.

(21) Appl. No.: 14/554,011

(22) Filed: Nov. 25, 2014

(65) Prior Publication Data
US 2015/0143916 A1    May 28, 2015

Related U.S. Application Data

(60) Provisional application No. 61/908,192, filed on Nov. 25, 2013.

(51) Int. Cl.
| | | |
|---|---|---|
| *G01N 29/04* | (2006.01) | |
| *G02B 27/00* | (2006.01) | |
| *G02B 1/11* | (2015.01) | |
| *G01N 19/04* | (2006.01) | |
| *B23K 26/142* | (2014.01) | |
| *G01N 29/24* | (2006.01) | |
| *B23K 26/16* | (2006.01) | |
| *G02B 1/18* | (2015.01) | |

(Continued)

(52) U.S. Cl.
CPC ............ *G02B 27/0006* (2013.01); *G02B 1/11* (2013.01); *B23K 26/142* (2015.10); *B23K 26/146* (2015.10); *B23K 26/16* (2013.01); *G01N 19/04* (2013.01); *G01N 29/2418* (2013.01); *G01N 2021/8472* (2013.01); *G01N 2291/0231* (2013.01); *G01N 2291/267* (2013.01); *G02B 1/18* (2015.01)

(58) Field of Classification Search
CPC ..... G01N 2291/0231; G01N 2291/267; G01N 29/2418; G02B 1/11; G02B 1/18; G02B 27/0006; B23K 26/142; B23K 26/146; B23K 26/16
USPC ........................ 73/800, 588, 842; 359/509
See application file for complete search history.

(56) References Cited

U.S. PATENT DOCUMENTS

| | | | | |
|---|---|---|---|---|
| 6,057,003 A | * | 5/2000 | Dulaney | ................. B05D 3/06 427/331 |
| 7,509,876 B1 | * | 3/2009 | Sokol | ..................... G01N 19/04 73/150 A |

(Continued)

*Primary Examiner* — Jonathan Dunlap
(74) *Attorney, Agent, or Firm* — Benesch, Friedlander, Coplan & Aronoff LLP

(57) ABSTRACT

Methods, systems, and apparatuses are disclosed for the protection of optical components used during laser bond inspection. In one embodiment, an optic surface wetting enhancement is provided on a protective optic to assist in forming a substantially flat film of transparent liquid from transparent liquid applied to a surface of a protective optic. A flat film of transparent liquid on a surface of a protective optic may be used to retain debris and effluent backscatter produced during a laser bond inspection process.

11 Claims, 9 Drawing Sheets

(51) Int. Cl.
*B23K 26/146* (2014.01)
*G01N 21/84* (2006.01)

(56) References Cited

U.S. PATENT DOCUMENTS

| | | | | |
|---|---|---|---|---|
| 7,641,349 B1* | 1/2010 | Chrobak | | G02B 5/0891 |
| | | | | 359/845 |
| 7,735,377 B1* | 6/2010 | Sokol | | G01N 19/04 |
| | | | | 73/827 |
| 7,770,454 B2* | 8/2010 | Sokol | | G01N 29/2412 |
| | | | | 73/588 |
| 7,775,122 B1* | 8/2010 | Toller | | G01N 19/04 |
| | | | | 73/760 |
| 8,132,460 B1* | 3/2012 | Toller | | G01N 29/2412 |
| | | | | 73/588 |
| 8,156,811 B2* | 4/2012 | Toller | | G01N 29/043 |
| | | | | 73/588 |
| 8,785,814 B1* | 7/2014 | Toller | | B23K 26/16 |
| | | | | 219/121.72 |
| 8,899,761 B2* | 12/2014 | Tonar | | 359/509 |
| 2005/0120803 A1* | 6/2005 | Sokol | | G01N 29/2412 |
| | | | | 73/801 |
| 2007/0271841 A1* | 11/2007 | Bissonnette | | A01C 1/02 |
| | | | | 47/61 |
| 2008/0257048 A1* | 10/2008 | Walters | | G01N 29/043 |
| | | | | 73/588 |
| 2009/0098409 A1* | 4/2009 | Yamada | | B29D 11/00865 |
| | | | | 428/702 |
| 2010/0245821 A1* | 9/2010 | Corbett | | G01N 21/03 |
| | | | | 356/342 |
| 2014/0147627 A1* | 5/2014 | Aizenberg | | A61L 15/24 |
| | | | | 428/141 |
| 2014/0220306 A1* | 8/2014 | Uchida | | B29C 37/0053 |
| | | | | 428/172 |
| 2015/0259570 A1* | 9/2015 | Matsuoka | | C09D 7/12 |
| | | | | 524/588 |

* cited by examiner

PRIOR-ART

PROTECTION OF LASER BOND INSPECTION OPTICAL COMPONENTS

CROSS-REFERENCE TO RELATED APPLICATIONS

This application claims priority from U.S. Provisional Patent Application No. 61/908,192, filed on Nov. 25, 2013, which is incorporated by reference herein in its entirety.

BACKGROUND

Laser bond inspection (LBI) may be used for non-destructive inspection of structures assembled with adhesive bonds. LBI typically involves depositing laser energy onto the front surface of a bonded article, thereby generating compression waves that reflect off of a back surface of the bonded article as tensile waves. The tensile waves provide stresses that interrogate the strength or relative quality of a bond.

Similar to LBI is laser induced bond delamination, which generally includes laser processing a bonded structure to intentionally induce defects in one or more bonds contained in the bonded structure.

With reference to FIG. 1, a general LBI and bond delamination process 100 is illustrated. In each of these applications, before laser processing a workpiece, an overlay coating 112, which may be substantially opaque to laser beam 102, may be applied to a front surface 106 of a workpiece being processed. An additional layer 110, which may be substantially transparent to laser beam 102, may be applied over opaque overlay 112, or directly onto workpiece surface 106 (i.e., no opaque overlay coating is applied). Opaque overlay 112 may include, without limitation, tape, paint, or a liquid erosion-resistant coating as described in U.S. Pat. No. 7,268,317, which is incorporated herein by reference in its entirety. Transparent overlay 110 may include, but is not limited to, water, water-based solution, other noncorrosive liquids, glass, sodium silicate, fused silica, potassium chloride, sodium chloride, polyethylene, fluoroplastics, nitrocellulose, and mixtures thereof.

Laser pulse 102 passes through transparent overlay 110 and strikes opaque overlay 112, causing a portion of opaque overlay 112 to vaporize. The vapor absorbs the remaining laser energy and produces a rapidly expanding plasma plume 118. Since expanding plasma 118 is confined momentarily between workpiece surface 106 and transparent overlay 110, a rapidly rising high-pressure shock wave 108 is created which propagates into material 104. Compressive wave 108 propagates through material 104 and may reflect off back surface 116 of material 104 as a tensile wave (not shown) to interrogate bond 114, or may be used to introduce defects into bond 114.

An LBI process often produces debris and effluent backscatter from target sources, contaminating nearby optics such as a final focusing lens, and other optical components of LBI equipment. In some instances, these contaminants accumulate on optical components, such as lenses, during LBI, and absorb laser radiation which may cause damage to optical components. Thus, what is needed is a simple, low-cost solution to protect laser bond inspection optical components.

SUMMARY

In one embodiment, a protective optic for use in a laser bond inspection system to protect components of the laser bond inspection system from effluent backscatter and debris produced during a laser bond inspection process is provided, the protective optic comprising: a first surface and a second surface opposite each other, the first surface and the second surface comprising a central portion configured to transmit a laser beam from a laser beam delivery system of the laser bond inspection system, the second surface oriented nearer the laser beam delivery system, the first surface comprising an optic surface wetting enhancement modification such that the first surface is configured to support a transparent liquid on the first surface which is effective to retain the effluent backscatter and the debris.

In another embodiment, a laser bond inspection system having a protective optic with enhanced surface wetting for protecting components of the laser bond inspection system from effluent backscatter and debris during a laser bond inspection process is provided, the laser bond inspection system comprising: (1) a laser configured to produce a laser beam; (2) a laser beam delivery system, the laser beam delivery system configured to deliver the laser beam from the laser source to an inspection head, the laser beam delivery system comprising at least one of: one or more mirrors, one or more optical fibers, and an articulated arm; (3) an inspection head, the inspection head configured to output the laser beam to a workpiece surface, the inspection head comprising: a housing; a first output to output the laser beam; at least one second output configured to output at least one of: a transparent overlay, and a transparent liquid; a final focusing optic; and one or more evacuation ports for removing the transparent liquid; and (4) a protective optic for protecting components of the laser bond inspection system within the inspection head housing from effluent backscatter and debris during a laser bond inspection process, the protective optic comprising: a first surface and a second surface opposite each other, the first surface and the second surface comprising a central portion configured to transmit a laser beam from a laser beam delivery system, the second surface oriented nearer the laser beam delivery system, the first surface comprising an optic surface wetting enhancement modification such that the first surface is configured to support the transparent liquid on the first surface which is effective to retain the effluent backscatter and the debris.

In another embodiment, a method for laser bond inspection is provided, the method comprising: wetting at least one surface of a protective optic comprising an optic surface wetting enhancement with a transparent liquid; forming a substantially flat film of the transparent liquid; transmitting a laser through at least a transparent portion of the protective optic and the substantially flat film of the transparent liquid to lase a surface of a workpiece for laser bond inspection; lasing at least one of: a transparent overlay, and an opaque overlay on the workpiece surface to produce a plasma plume for laser bond inspection; retaining effluent backscatter or debris produced by the plasma plume in the substantially flat film of the transparent liquid; and evacuating at least a portion of the substantially flat film of the transparent liquid from the at least one surface of the protective optic having the optic surface wetting enhancement.

In one embodiment, the smooth coverage of a transparent liquid on the protective optic surface allows for the laser inspection head to be used in various orientations.

BRIEF DESCRIPTION OF THE DRAWINGS

The accompanying figures, which are incorporated in and constitute a part of the specification, illustrate various example systems and methods, and are used merely to illustrate various example embodiments.

DETAILED DESCRIPTION

Figure 1:
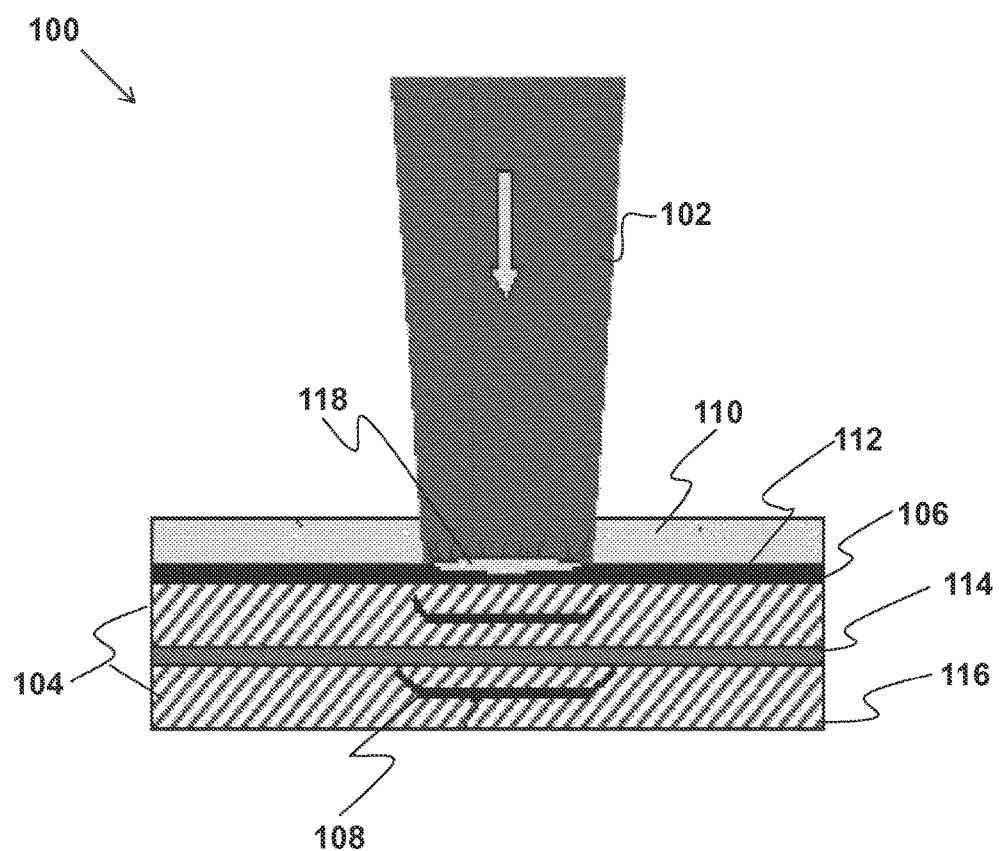
FIG. 1 illustrates a schematic of an LBI application.
Figure 2:
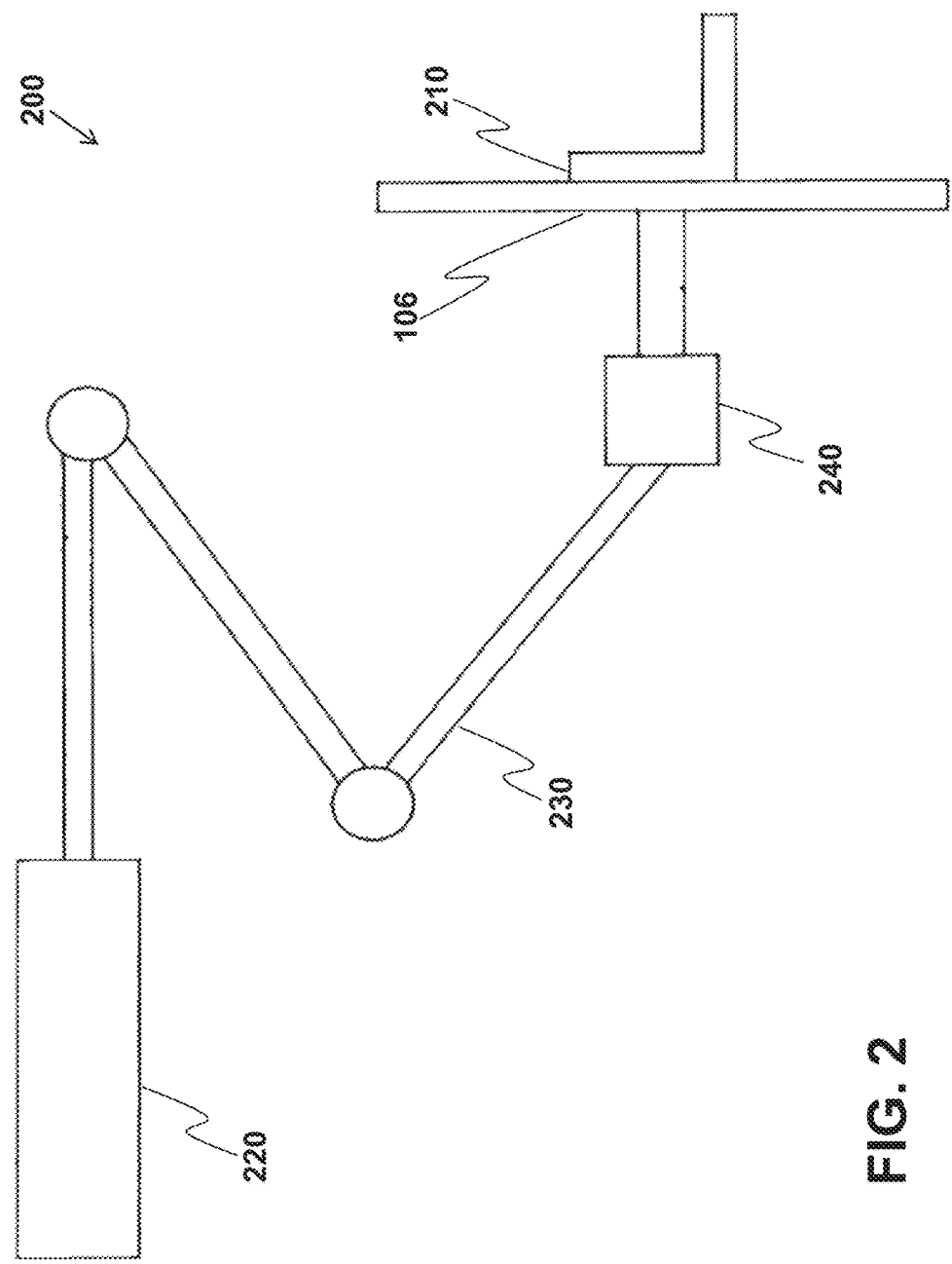
FIG. 2 illustrates one embodiment of an LBI system.

The embodiments claimed herein disclose using a protective optic with a laser bond inspection (LBI) system. With reference to FIG. 2, an LBI system 200 for laser bond inspection is provided. In one embodiment, LBI system 200 may be used for LBI of a bonded article 210. System 200 comprises: a laser 220; a laser beam delivery system 230; and an inspection head 240.

In one embodiment, laser 220 may comprise, for example, a neodymium glass laser, such as, for example, those manufactured by LSP Technologies, Inc., a YAG laser, a YLF laser, or any other solid-state crystal material, in either a rod or a slab gain medium. Laser 220 may be configured to deliver laser pulses 102 having a pulse energy of between about 3 J and about 50 J (at the output of the final amplifier module), a wavelength of about 1 µm, and a pulse width of between about 70 ns and 300 ns, and further being configured to deliver the laser pulses 102 in a low-high-low or probe-pump-probe pulse energy sequence (i.e., a first laser pulse 102 having a first energy, a second laser pulse 102 having a second energy that is greater than the first energy but less than an energy required to break a properly constructed or "good" bond, and a third laser pulse 102 having an energy which is approximately the same as the first pulses' energy), as described and illustrated in U.S. Pat. Nos. 7,770,454 and 8,156,811. Beam diameter for LBI is selected as a compromise between the need to have a large area for planar wave generation and a reasonable sized beam for the inspection of small zones in the object. A beam size of about 10.0 mm is a suitable compromise. The use of a large diameter laser beam of several mm or more generates suitable internal stress for the evaluation of internal bonds and avoids surface spallation of a bonded article under LBI. Fluence is a measure of energy delivered per unit area, and LBI uses fluence values ranging between about 4 J/cm$^2$ to about 6 J/cm$^2$ for interrogation of weak bonds, while medium strength bonds fail around about 16 J/cm$^2$. Further configurations of laser 220 may include those described and illustrated in U.S. Pat. Nos. 7,770,454 and 8,156,811.

In one embodiment, laser beam delivery system 230 may comprise, for example, at least one of: (a) one or more mirrors; (b) an articulated arm; and (c) one or more fiber optics (also referred to herein as optical fibers), and includes a laser beam delivery systems described and illustrated in U.S. Pat. Nos. 7,770,454 and 8,156,811. In one embodiment, where laser beam delivery system 230 is one or more mirrors, the beam 102 may be directed to the surface 106 of bonded article 210. In alternative embodiments, where laser beam delivery system 230 is an articulated arm and/or a fiber optic, laser beam delivery system 230 may be operatively connected to inspection head 240.

Figure 3:
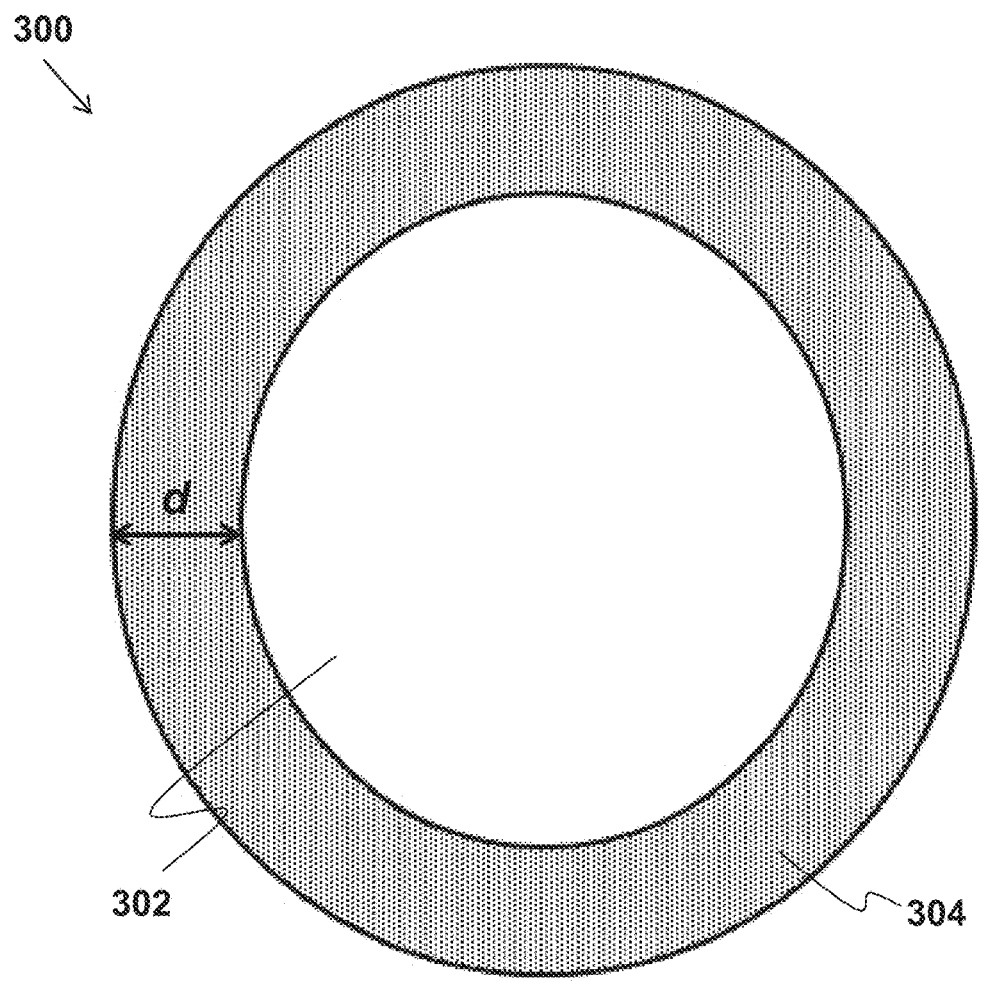
FIG. 3 illustrates one embodiment of a protective optic used in an LBI system.

With reference to FIG. 3, an example protective optic 300 for use in, e.g., inspection head 240 of LBI system 200 is illustrated. Protective optic 300 may comprise a substantially transparent region 302 surrounded by a frosted region 304 around the perimeter of protective optic 300. In one embodiment, protective optic 300 may be a lens or window of a material configured to transmit light such as glass, transparent polymeric material, and the like. Frosted region 304 appears "frosted" due to the intentional introduction of multiple defects and multiple impurities on one or more surfaces of protective optic 300. Such defects and impurities may be pits or pores created in a surface of protective optic 300. A high density of pits and pores on a surface creates a rough surface on protective optic 300 giving a "frosted" appearance. Multiple defects and impurities may be formed on protective optic 300 by mechanical abrasion processes, chemical etching, and the like. In one embodiment, frosted region 304 is formed by a mechanical abrasion process such as grit blasting or sandblasting where an abrasive media such as aluminum oxide is mixed with a high pressure gas stream to abrade a surface of protective optic 300 causing surface deformation. In another embodiment, frosted region 304 is formed by a chemical etching process where an acidic or caustic chemical etchant, such as sodium fluoride or hydrogen fluoride containing compounds, is applied to protective optic 300. Etching chemicals react with material of protective optic 300 to deform a surface of protective optic 300.

One or more surfaces of protective optic 300 may be coated with an anti-reflective (AR) coating to substantially reduce reflection of a beam 102 produced by laser 220 on protective optic 300 which could cause unwanted feedback in laser 220. In one embodiment, a normal AR coating is used on protective optic surface 300. In another embodiment, a hydrophilic AR coating is used on a surface of protective optic 300. Target side surface 301a of protective optic 300 may not require an AR coating, as a transparent liquid applied to target side surface 300a may substantially reduce reflections at the liquid/protective optic 300 interface.

In one embodiment, frosted region 304 may be in the form of an annulus or annular ring on an outer perimeter of a circular shaped protective optic 300. However, frosted region 304 and protective optic 300 are not limited to a circular shape. Additionally, frosted region 304 is not limited to being formed on an outer perimeter of protective optic 300. Frosted region 304 may be formed on a substantial portion or an entire optical surface of protective optic 300. The inside diameter d of frosted region 304 may be varied to optimize a formation of a nearly optically flat, wetted surface of a liquid applied on a target side surface of protective optic 300 which is a surface closest to a target surface, e.g., 106. While not bound to any particular theory, an element for establishing and maintaining a nearly optically flat liquid film is a surface tension of the liquid. Water, as an example liquid, has a strong surface tension and due to strong cohesive forces between water molecules will naturally try to form into a sphere when there are no outside forces acting upon it. On a nonpolar surface such as optical glass (e.g. protective optic 300), water droplets will naturally try to form into spherical droplets while the force of gravity acts to slightly flatten the spherical droplets making them less spherical. Due to low adhesion forces between the water droplets and the nonpolar surface, the natural tendency of water and its strong cohesive force between water molecules is to minimize its contact with such a surface such that water will separate into spherical drops or beads instead of uniformly wetting the surface in a nearly optically flat, thin film (i.e. substantially flat). In a surface with a high density of surface defects (e.g. frosted region 304), the pores and pits of this region act as capillaries, sourcing water from the surrounding regions (e.g. substantially transparent region 302) toward frosted region 304 by a capillary action. Frosted region 304 also increases adhesion forces of the surface such that the cohesive forces between the water molecules are weakened, and the increased adhesion of frosted area 304 prevents water from substantially transparent region 302 from flowing away, allowing a thin film of water to remain in place during an LBI process, and forming a substantially flat, thin film on a target-side surface of protective optic 300.

Figure 4:
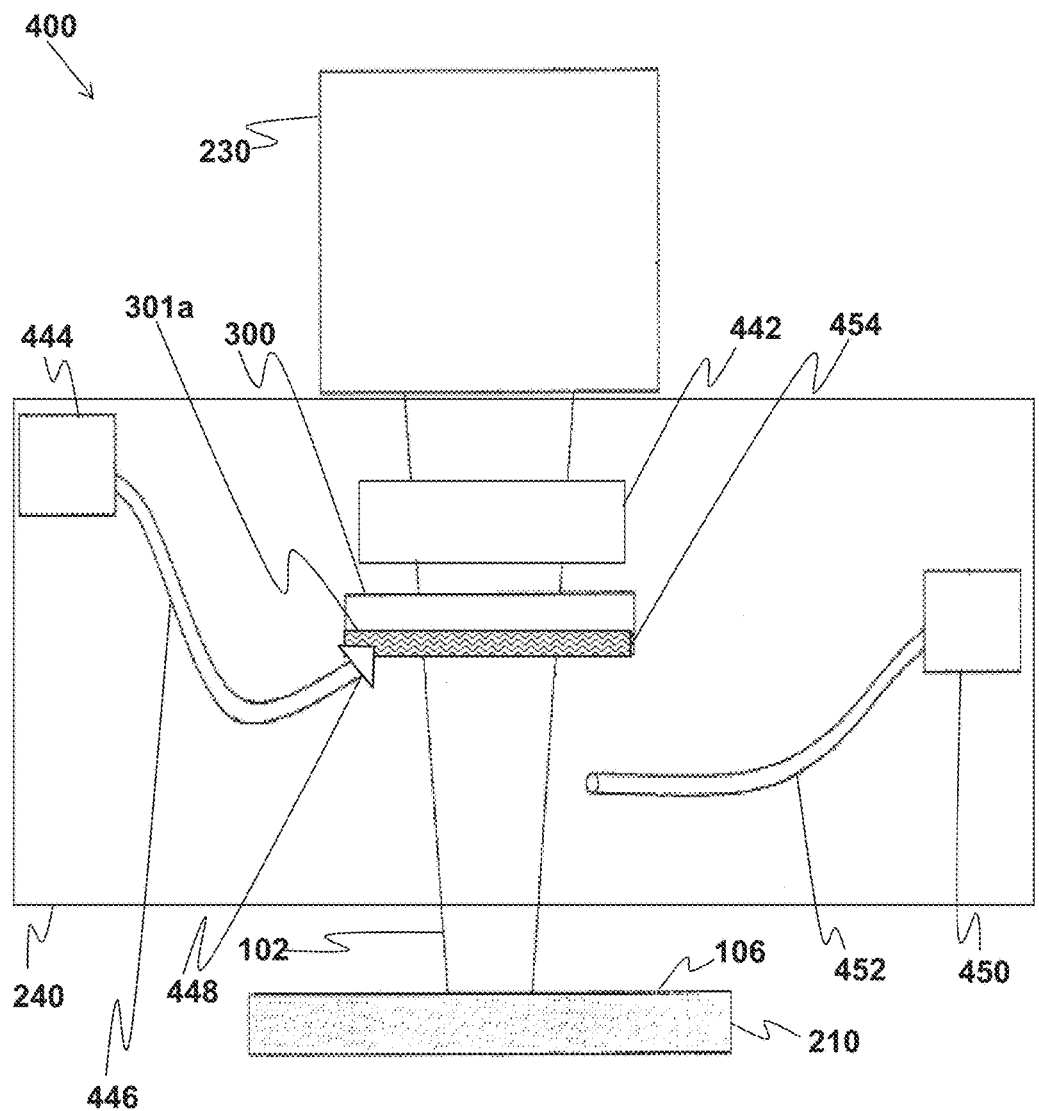
FIG. 4 illustrates one embodiment of an LBI system using a protective optic.

With reference to FIG. 4, one embodiment 400 of LBI system 200 using protective optic 300 is illustrated. In one embodiment, a laser beam 102 from laser 220 delivered via laser beam delivery system 230 passes through a final focusing optic 442 and protective optic 300 in inspection head 240 before contacting target surface 106 of bonded article 210. Final focusing optic 442 and protective optic 300 may be combined into one optic such that substantially transparent region 302 and frosted region 304 are incorporated onto a surface final focusing optic 442 in addition to other optical properties of final focusing optic 442.

Inspection head 240 may additionally include one or more liquid delivery mechanisms 444. Generally, one or more liquid delivery mechanisms 444, applicator tubes 448, and nozzles 448 may be referred to herein collectively as an "output," or "liquid output," for example, to output a transparent liquid. Liquid delivery mechanisms 444 may be configured on inspection head 240 to provide either of a liquid transparent overlay 110 or transparent liquid 454. Each of one or more liquid delivery mechanisms 444 may be adapted to perform a specified function. For example, one liquid delivery mechanism 444 may be configured to deliver only a liquid transparent overlay 110 to a surface of a workpiece, while another liquid delivery mechanism 444 may be adapted to provide only a transparent liquid 454 to a surface 301a of protective optic 300. In one embodiment, liquid delivery mechanism 444 may be a pump used to supply a liquid such as water via a liquid applicator tube 446 for use as transparent liquid 454. In the illustrated embodiment, a transparent liquid 454 may be applied to target surface side 301a of protective optic 300 by liquid delivery mechanism 444 through liquid applicator tube 446. Liquid applicator tube 446 may be a rigid tube or a flexible tube. Liquid applicator tube 446 may be constructed of metal, glass, or a polymeric material. Liquid applicator tube 446 (and any "applicator tube" described in the present embodiments) may alternatively be any type of apparatus know in the art that is capable of transferring or allowing a flow of liquid from liquid delivery mechanism 444 to a surface of the optic (e.g., a machine channel). In one embodiment, liquid applicator tube 446 has a nozzle 448 on one end to control a direction or characteristics of fluid flow of liquid in liquid applicator tube 446. In one embodiment, nozzle 448 directs and controls fluid flow of transparent liquid 454 from liquid delivery mechanism 444 and outputs transparent liquid 454 near a perimeter of protective optic 300. In another embodiment, liquid delivery mechanism 444 may have one liquid applicator tube 446 positioned near a perimeter of protective optic 300, and one liquid applicator tube 446 positioned near a center of protective optic 400 to provide a transparent liquid 454 to target side surface 301a of protective optic 300.

Transparent liquid 454 may be water or any other liquid that is not harmful to protective optic 300 and is substantially transparent to laser beam 102. In one embodiment, transparent liquid 454 contains a surfactant that reduces surface tension to encourage formation of a flat liquid film on target side surface 301a when transparent liquid 454 is applied to protective optic 300.

In various embodiments, one or more optic surfaces of protective optic 300 may be contacted with one or transparent liquids 454. The one or more transparent liquids 454 may be configured to protect one or more optic surfaces of protective optic 300. The one or more transparent liquids 454 may include a solvent, such as water or an organic solvent. The one or more transparent liquids 454 may be configured to wet the one or more optic surfaces. For example, the one or more transparent liquids 454 may be selected for a hydrophobic or hydrophilic character in accord with a corresponding hydrophobic or hydrophilic character of the one or more optic surfaces (i.e. 301a) to provide a wetting action—that is, liquid selection may be based on optic surface characteristics. The one or more transparent liquids 454 may be selected for hydrophobic of hydrophilic character based on the solvent selected—that is, liquid selection may be based on solvent selection. The wetting action of one or more transparent liquids 454 may also be modified by including a wetting agent, such as a surfactant.

Inspection head 240 may additionally include one or more evacuation mechanisms 450. In one embodiment, evacuation mechanism 450 is a vacuum pump. Evacuation mechanism 450 may be capable of removing and exhausting solid particles, liquids, gases, or any combination thereof which may specifically include: transparent liquid 454 from target side surface 301a of protective optic 300, a liquid transparent overlay 110 applied to target surface 106 of bonded article 210, gas produced during LBI, effluent backscatter, and debris produced during LBI. Evacuation mechanism 450 includes an evacuation tube 452. In one embodiment, evacuation tube 452 may be located between protective optic 300 and target surface 106 of bonded article 210. Evacuation tube 452 may include hardware such as a nozzle or port to direct or modify vacuum flow or vacuum direction. As referred to herein, an "evacuation port" may include evacuation mechanism 450 and evacuation tube 452, and be configured to remove material via suction or vacuum.

In one embodiment 400, LBI system 200 with protective optic 300 may be used for LBI of bonded article 210. Prior to laser beam 102 being applied to surface 106 of bonded article 210, liquid delivery mechanism 444 provides a transparent liquid 454 via liquid applicator tube 446 to target side surface 301a of protective optic 300. A control system (not shown) of LBI system 200 may automatically facilitate a process of wetting protective optic 300, or a wetting process may be initiated manually by a button push or similar device. After target side surface 301a of protective optic 300 is wetted with transparent liquid 454, and transparent liquid 454 is formed into a nearly optically flat, thin film of transparent liquid 454, liquid application mechanism 444 may be turned off to stop a flow of transparent liquid 454 from liquid application mechanism 444 to protective optic 300. Laser 220 may produce a laser beam 102 delivered via laser beam delivery system 230 to inspection head 240. Inspection head 240 may include and output which may be configured to output laser beam 102 from inspection head 240 towards a workpiece surface 106. Inside inspection head 240, laser beam 102 passes through a final focusing optic 442, protective optic 300, and transparent liquid 454 before contacting surface 106 of bonded article 210. A high pressure shockwave 108 and plasma plume 118 generated by a vaporization of opaque layer 112 may generate debris and effluent backscatter. Debris may include portions of vaporized opaque layer 112 and surface 106. Effluent backscatter may include scattered portions of transparent liquid overlay layer 110 caused by the shockwave 108 and plasma plume 118 created during an LBI process. Transparent liquid 454 prevents accumulation of debris and effluent backscatter on protective optic 300. Debris and effluent backscatter may accumulate in, and be retained within transparent liquid 454. Transparent liquid 454 along with protective optic 300 prevents accumulation of debris and effluent backscatter on final focusing optic 442 and other optical components in inspection head 240. After an LBI process concludes, transparent liquid 454 may be removed from protective optic 300 via a vacuum stream in evacuation tube 452 produced by evacuation mechanism 450—that is, transparent liquid 454 retaining debris and effluent backscatter may be evacuated through an evacuation port after an LBI process. In one embodiment, transparent liquid 454 remains in place on protective optic 300 during LBI for an entire LBI operation. In another embodiment, transparent liquid 454 is removed by evacuation mechanism 450 after an LBI process for each target area. In one embodiment, evacuation of transparent liquid 454 by evacuation mechanism 450 may be initiated automatically by a control system (not shown) of LBI system 200. In another embodiment, evacuation of transparent liquid 454 may be initiated manually by a button push or similar device.

Figure 5:
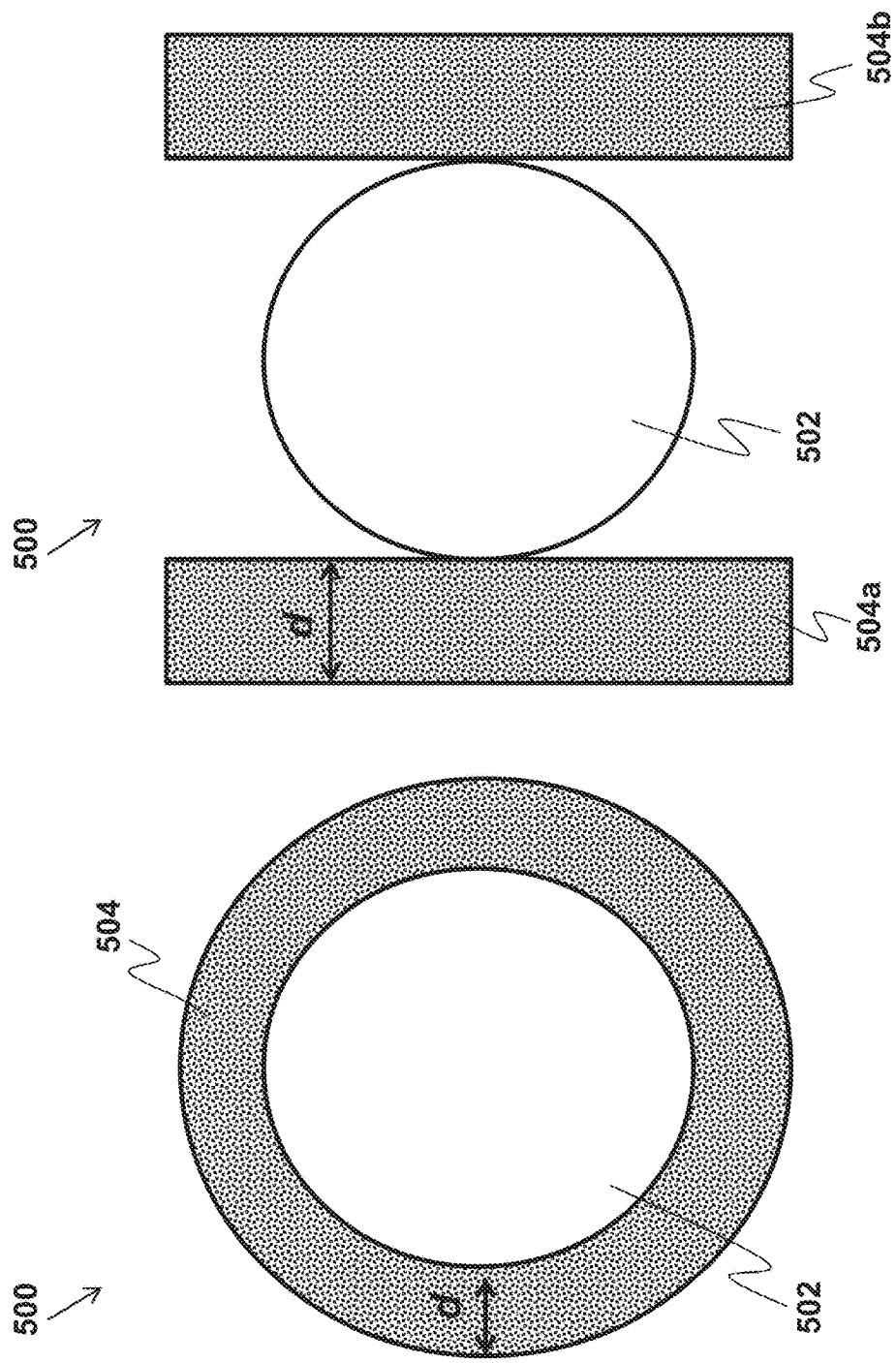
FIG. 5a illustrates an alternative embodiment of a protective optic used during LBI.
FIG. 5b illustrates an alternative embodiment of a protective optic used during LBI.

With reference to FIGS. 5a and 5b, an alternative embodiment of protective optic 500 for use in, e.g., inspection head 240 of LBI system 200 is provided. Protective optic 500 may comprise a substantially transparent aperture region 502 surrounded by a wicking material region 504 around a perimeter of protective optic 500. Protective optic 500 may be of a material configured to transmit light such as glass, transparent polymeric material, and the like. Wicking material region 504 may contain a material whose properties encourage a capillary action of transparent liquid 454 over a surface of protective optic 500, such that when a transparent liquid 454 contacts wicking material region 504, transparent liquid 454 in substantially transparent aperture region 502 is drawn towards wicking material region 504. Wicking device region 504 may be substantially rougher than transparent region 502. In addition, porous material characteristics of wicking material region 504 may readily attract, and absorbs water. Wicking material region 504 may be of a material such as, but not limited to: a cloth material, cotton, steel wool, wire mesh, carbon fiber mesh, and the like, or include a rough surface. In one embodiment, wicking device region 504 may be formed by securing material to protective optic 500 by an adhesive or the like. In another embodiment, wicking device region 504 may be integrated in protective optic 500 through a manufacturing process, whereby wicking device region 504 may be embedded in protective optic 500 during the manufacturing process.

One or more surfaces of protective optic 500 may be coated with an anti-reflective (AR) coating to prevent reflection of a beam 102 produced by laser 220 on protective optic 500 which could cause unwanted feedback in laser 220. In one embodiment, a normal AR coating may is used on surfaces of protective optic 500. In another embodiment, a hydrophilic AR coating is used on a surface of protective optic 500.

In one embodiment, wicking material region 504 is in the form of an annulus or annular ring on an outer perimeter of a circular shaped protective optic 500 as in FIG. 5a. However, wicking material region 504 and protective optic 500 are not limited to a circular shape.

FIG. 5b illustrates a different embodiment with a parallel rail configuration of wicking material region 504. In this embodiment, wicking material region 504 comprises two wicking material strips 504a and 504b which are separated by substantially transparent aperture 502. Transparent liquid 454 is drawn toward wicking material strips 504a and 504b such that a nearly optically flat, thin film of transparent liquid 454 covers substantially transparent aperture 502.

As used herein, an optic surface wetting enhancement modification may include any and all of the aforementioned embodiments used to form of a substantially flat film of transparent liquid 454 on one or more surfaces of protective optic 300. A surface wetting enhancement modification may include, but is not limited to: a plurality of surface deformations, a wicking material, a hydrophilic coating, and a wetting agent or surfactant added to transparent liquid 454.

Figure 6:
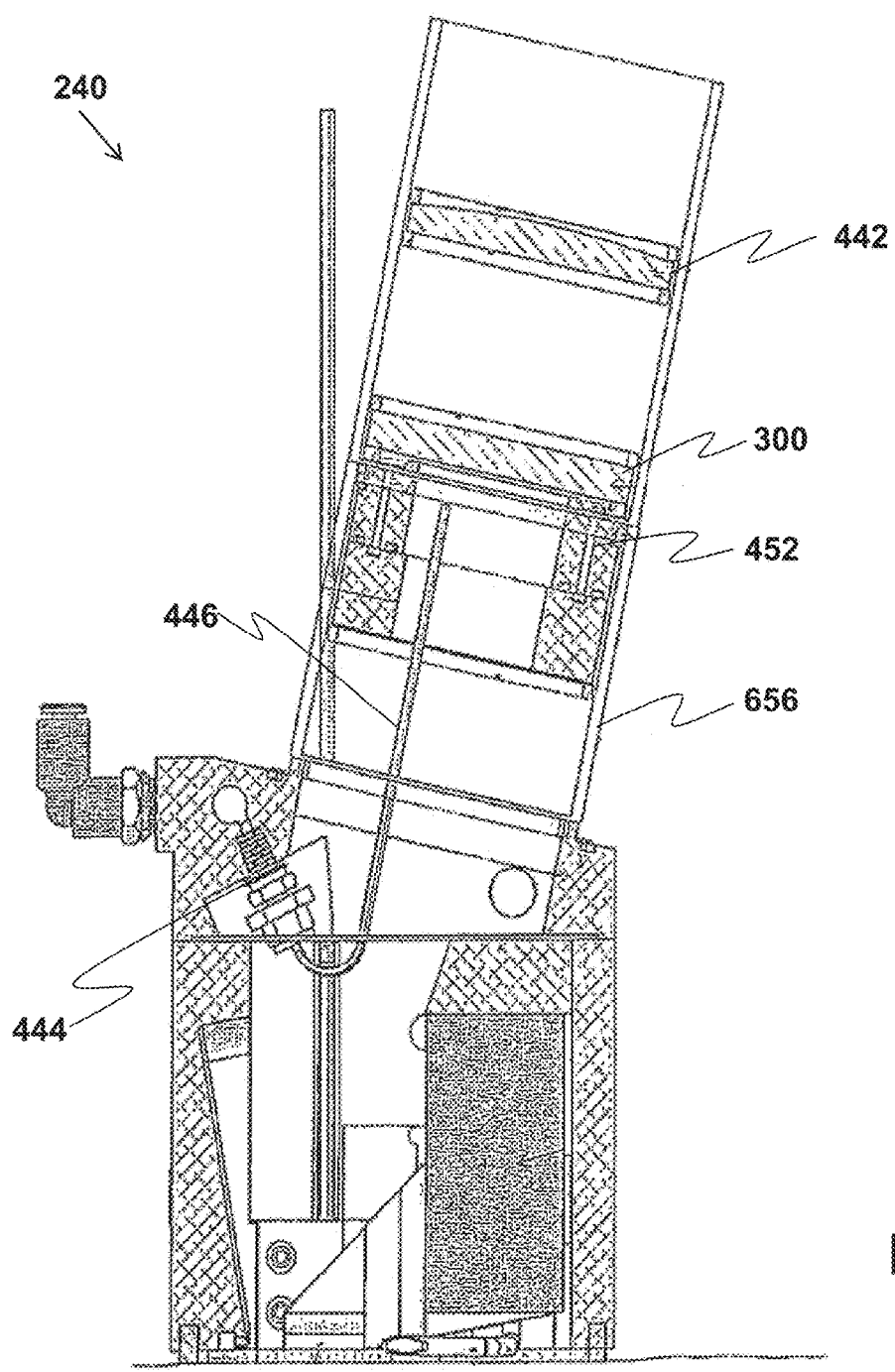
FIG. 6 illustrates an example schematic embodiment of a protective optic within a laser inspection head.

With reference to FIG. 6, a schematic view of one embodiment of laser inspection head 240 that facilitates delivery of laser beam 102 from articulated arm of laser beam delivery system 230 to a bonded structure surface 106 is illustrated. Laser inspection head 240 includes a housing 656. Final focusing optic 442 protected by protective optic 300 is disposed within housing 656. Further, liquid applicator tube 446, liquid applicator mechanism 444, evacuation tube 452, and evacuation mechanism (not shown) are also disposed within housing 656.

Figure 7:
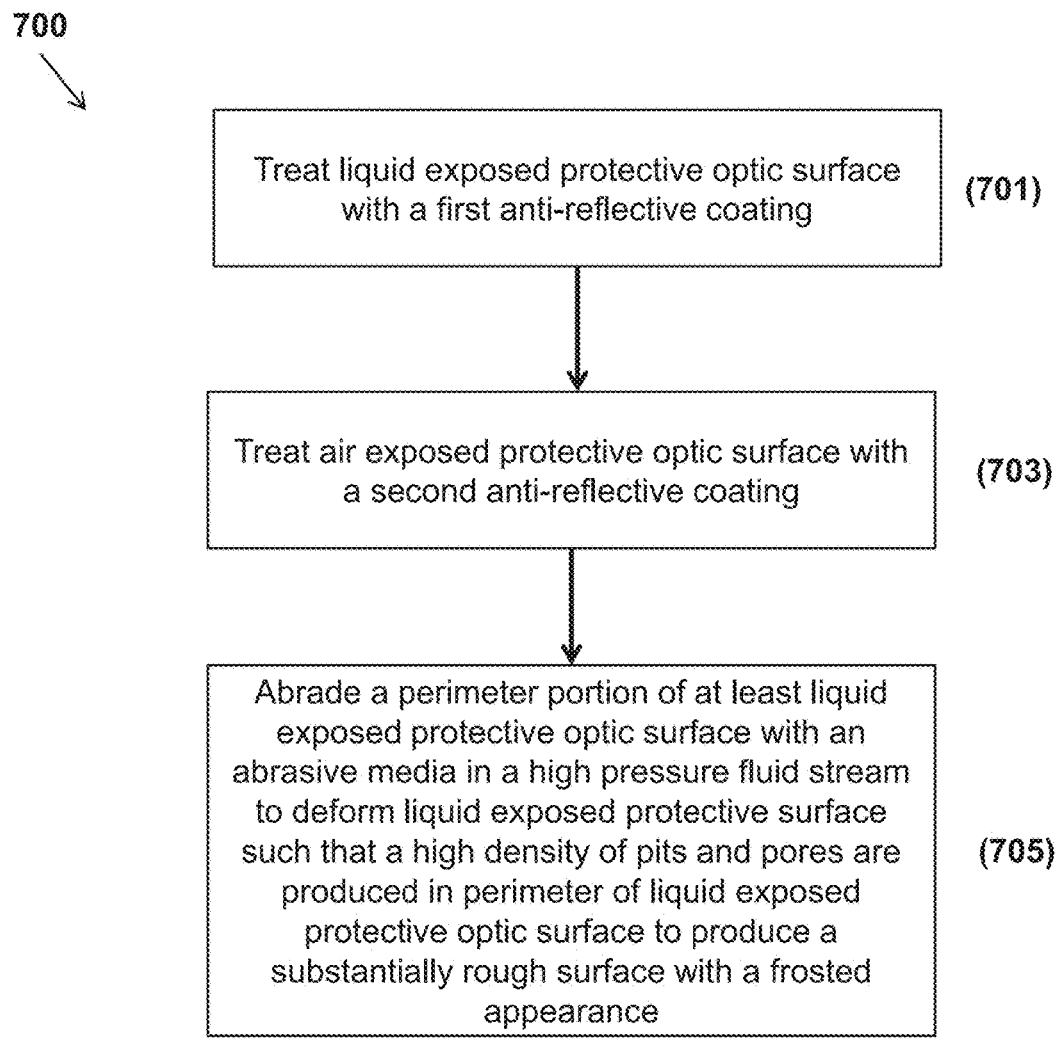
FIG. 7 illustrates a flowchart depicting one embodiment of a method for producing a protective optic used during LBI.

With reference to FIG. 7, a flowchart depicting one embodiment of a method 700 for producing a protective optic for use in an LBI system is provided. In step (701), a liquid exposed protective optic surface is treated with a first AR coating. The liquid exposed protective optic surface is the target side surface 301a of protective optic 300. In step (703), an air exposed protective optic surface—that is a surface nearer to LBI components in inspection head 240— is treated with a second AR coating. Because of a difference in the index of refraction between air and liquids, first AR coating will be optimized to minimize reflections at liquid exposed protective surface depending on the transparent liquid 454 used in system 400, while second AR coating will be optimized to minimize reflections at air exposed protective surface. A custom AR coating with hydrophilic properties may be employed on one or both liquid exposed protective surface, and air exposed protective surface to increase a sheeting effect of transparent liquid 454 to produce a nearly optically flat, thin film of transparent liquid 454. In step (705), a perimeter portion of at least liquid exposed protective optic surface is abraded with an abrasive media through a high pressure gas stream to deform liquid exposed protective surface such that a high density of pits and pores are produced in liquid exposed protective optic surface to produce a substantially rough surface with a frosted appearance.

Figure 8:
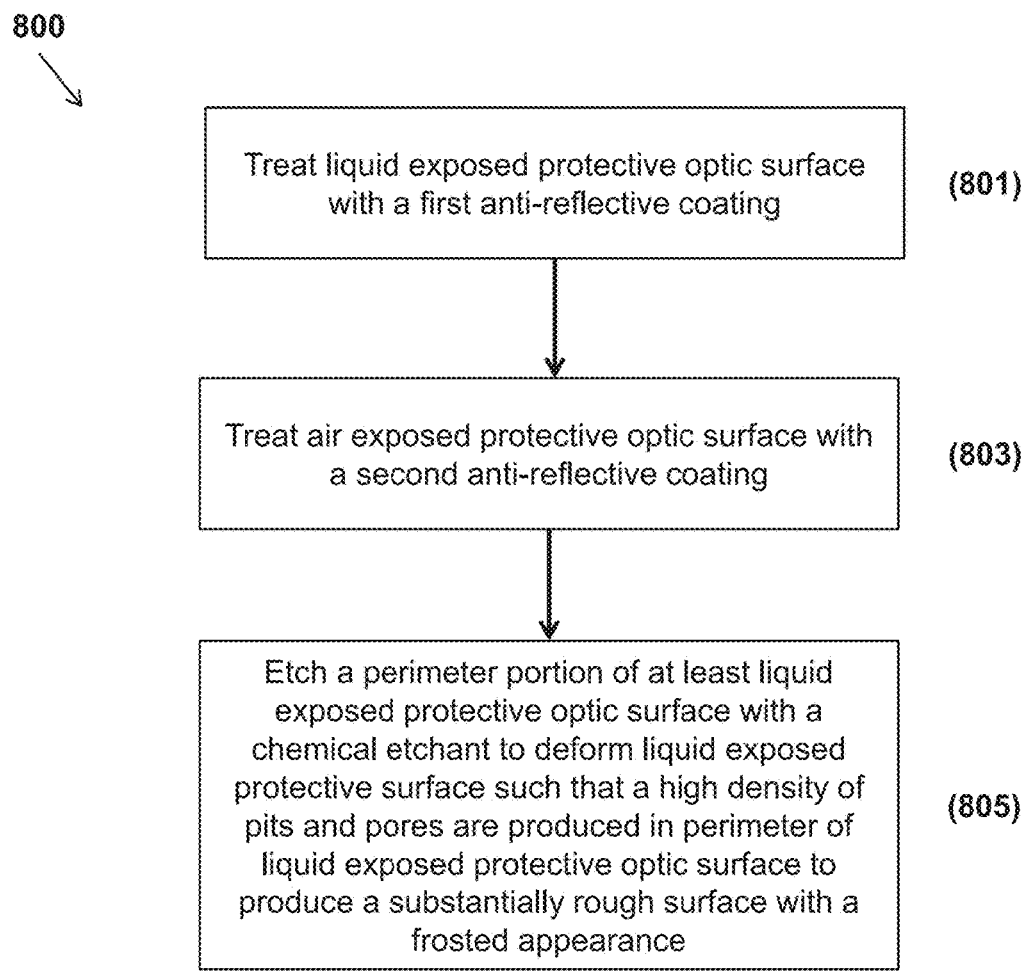
FIG. 8 illustrates a flowchart depicting an alternative embodiment of a method for producing a protective optic used during LBI.

With reference to FIG. 8, a flowchart depicting another embodiment of a method 800 for producing a protective optic for use in an LBI system is provided. In step (801), a liquid exposed protective optic surface is treated with a first AR coating. The liquid exposed protective optic surface is the target side surface 301a of protective optic 300. In step (803), an air exposed protective optic surface is treated with a second AR coating. Because of a difference in the index of refraction between air and liquids, first AR coating will be optimized to minimize reflections at liquid exposed protective surface depending on the transparent liquid 454 used in system 400, while second AR coating will be optimized to minimize reflections at air exposed protective surface. A custom AR coating with hydrophilic properties may be employed on one or both liquid exposed protective surface and air exposed protective surface to increase a sheeting effect of transparent liquid 454 to produce a nearly optically flat, thin film of transparent liquid 454. In step (805), a perimeter portion of at least liquid exposed protective optic surface is etched with a chemical etchant to deform liquid exposed protective surface such that a high density of pits and pores are produced in liquid exposed protective optic surface to produce a substantially rough surface with a frosted appearance.

Figure 9:
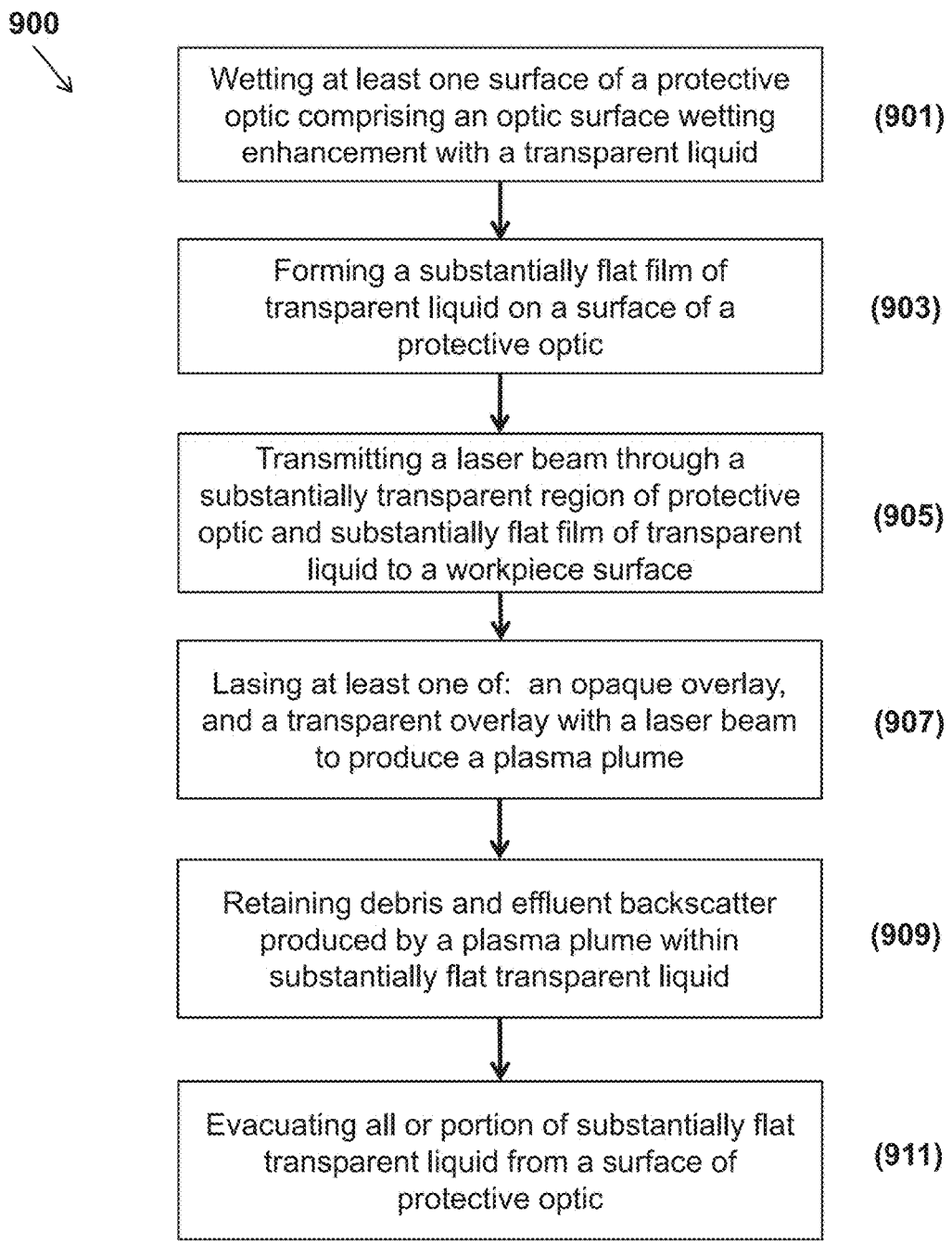
FIG. 9 illustrates a flowchart depicting one embodiment of a method for LBI using a protective optic.

With reference to FIG. 9, a flowchart illustrating an example method 900 for LBI using a protective optic is provided. In step (901), at least one surface (i.e. surface 301a) of protective optic 300 with an optic surface wetting enhancement is wetted with transparent liquid 454. In step (903), an optic surface wetting enhancement causes transparent liquid 454 to form into a substantially flat film of transparent liquid 454. In step (905), a laser beam 102 is transmitted through substantially transparent region 302 of protective optic 300 and substantially flat film of transparent liquid 454 to a workpiece surface 106. In step (907), laser beam 102 lases at least one of: an opaque overlay 112, and a transparent overlay 110 to produce plasma plume 118. In step (909) debris and effluent backscatter produced by plasma plume 118 may interacts with, and may be retained within substantially flat film of transparent liquid 454. In step (911), all or portion of substantially flat film of transparent liquid 454 covering protective optic 300 and debris and effluent backscatter contained therein is evacuated.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

As used in the specification and the claims, the singular forms "a," "an," and "the" include the plural. To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11.

What is claimed is:

1. An optic comprising:
   a first surface and a second surface opposite each other, the first surface and the second surface each having a transparent central portion configured to transmit a laser beam provided by a laser beam delivery system of a laser bond inspection system, the second surface oriented nearer the laser beam delivery system;
   a wicking material to support a transparent liquid within the transparent central portion on the first surface during a laser bond inspection process, wherein the wicking material is one of secured to the first surface of the optic by an adhesive and integrated into the optic such that the wicking material is embedded into the optic;
   wherein the wicking material at the first surface is located outside the transparent central portion of the first surface at a periphery of the transparent central portion of the first surface so as not to affect a transmission of the laser beam through the transparent central portion,
   wherein the wicking material is configured to draw the transparent liquid from the transparent central portion of the first surface toward the periphery of the first surface and cause the transparent liquid to form in a substantially flat film on the transparent central portion.

2. The optic of claim 1, wherein both the first surface and the second surface is coated with an anti-reflective (AR) coating.

3. The optic of claim 2, wherein the AR coating corresponds to a hydrophilic AR coating.

4. The optic of claim 1, wherein a capillary action of the wicking material draws the transparent liquid toward the wicking material, and an adhesive force between the wicking material and the transparent liquid causes the transparent liquid to form in the substantially flat film on the transparent central portion.

5. The optic of claim 4, wherein the wicking material is one of a cloth material, cotton, steel wool, wire mesh, and carbon fiber mesh.

6. The optic of claim 4, wherein the laser beam is transmitted through the transparent central portion of each of the first surface and the second surface and further through the transparent liquid to an article of interest during the laser bond inspection process.

7. The optic of claim 1, wherein the transparent liquid comprises one of water and an organic solvent.

8. A laser bond inspection system comprising:
a laser configured to produce a laser beam;
a laser beam delivery system configured to supply the laser beam to an inspection head, the laser beam delivery system comprising one of one or more mirrors, one or more optical fibers, and an articulated arm;
an inspection head configured to output the laser beam, the inspection head comprising: a housing, a first output to output the laser beam, a second output configured to output a transparent liquid, a final focusing optic and one or more evacuation ports for removing the transparent liquid, and
a protective optic configured to protect one or more components of the inspection head from effluent backscatter and debris during a laser bond inspection process, the protective optic comprising:
a first surface and a second surface opposite each other, the first surface and the second surface each having a transparent central portion configured to transmit the laser beam, the second surface oriented nearer the laser beam delivery system, the first surface;
a wicking material to support the transparent liquid on the first surface during the laser bond inspection process, wherein the wicking material is one of secured to the first surface of the protective optic by an adhesive and integrated into the optic such that the wicking material is embedded into the protective optic;
wherein the wicking material at the first surface is located outside the transparent central portion of the first surface at a periphery of the transparent central portion of the first surface so as not to affect a transmission of the laser beam through the transparent central portion,
wherein the wicking material provides an adhesive force and a capillary action at the periphery, wherein the capillary action at the periphery draws the transparent liquid from the transparent central portion toward the periphery, and the adhesive force at the periphery causes the transparent liquid to form in a substantially flat film on the transparent central portion.

9. The laser bond inspection system of claim 8, wherein both the first surface and the second surface of the protective optic is coated with an anti-reflective (AR) coating.

10. The laser bond inspection system of claim 8, wherein the laser beam is transmitted through the transparent central portion of each of the first surface and the second surface and further through the transparent liquid to an article of interest during the laser bond inspection process.

11. The laser bond inspection system of claim 8, wherein the transparent liquid comprises one of water and an organic solvent.

* * * * *